US00PP09784P

United States Patent [19]

Marshall

[11] Patent Number: Plant 9,784

[45] Date of Patent: Jan. 21, 1997

[54] "AUGUST WHITE" PEACH TREE

[76] Inventor: Richard J. Marshall, 6321 Ave. 376, Dinuba, Calif. 93618

[21] Appl. No.: 399,994

[22] Filed: Jan. 23, 1995

[51] Int. Cl.[6] ..... A01H 5/00

[52] U.S. Cl. ..... Plt./42.1

[58] Field of Search ..... Plt./42.1

[56] References Cited

U.S. PATENT DOCUMENTS

P.P. 4,865 7/1982 Armstrong ..... Plt./42.1

*Primary Examiner*—James R. Feyrer
*Attorney, Agent, or Firm*—Worrel & Worrel

[57] ABSTRACT

A new and distinct variety of peach tree which is somewhat remotely similar to the "Champagne" peach tree (U.S. Pat. No. P.P. 4,865) of which it is a sport, but from which it is distinguished by producing fruit which are mature for harvesting and shipment approximately eight (8) days to two weeks after the fruit produced by the "Champagne" peach tree and wherein the fruit has more flavor and a white flesh coloration.

1 Drawing Sheet

BACKGROUND OF THE NEW VARIETY

The present invention relates to a new and distinct variety of peach tree, which will hereinafter be denominated varietally as the "August White" peach tree, and, more particularly, to a peach tree which produces freestone fruit, which are mature for commercial harvesting and shipment approximately August 20 to August 31, or about eight (8) days to two (2) weeks after the fruit of "Champagne" peach tree, in the San Joaquin Valley of central California.

The discovery and commercialization of new plant varieties, particularly of new varieties of fruit trees, is a process which is fraught with risk, both to the developer as well as to others involved in the process. This is certainly the case in regard to new peach varieties, in part because of the multiplicity of existing peach varieties. The investment in time and expense required in such development is enormous and is entirely contigent upon the assessment of those involved in the process as to the value of the new variety for commercialization. If a positive assessment proves to be without foundation, the loss to those involved may be considerable. Accordingly, the development of new varieties of peach trees is frequently a slow and painstaking process designed to ensure that the initial positive assessment is well founded and thus minimize the risk of loss.

The new variety of peach tree of the present invention appears to be an attractive candidate for commercialization due to its distinctive characteristics, as will hereinafter be fully set forth.

ORIGIN AND ASEXUAL REPRODUCTION OF THE NEW VARIETY

The present variety of peach tree hereof was discovered by the inventor is a peach orchard which is located at Road 44 and Brewer Dr. near Dinuba in the San Joaquin Valley of central California. The inventor discovered the new variety as a sport of the "Champagne" peach tree U.S. Pat. No. P.P. 4,865) in August of 1993. In the spring of 1994, the inventor asexually reproduced the new variety by grafting scions of the new variety containing several buds, including vegetative and flower buds on six trees of Nemagard root stock to the new variety at Kingsburg in the San Joaquin Valley of central California. These scions of the new variety produced fruit in August of 1994 which has been observed by the inventor and has similarly been observed each year thereafter. The inventor has observed the asexually reproduced trees of the new variety and confirmed that they are in all respects identical to the originally discovered sport.

SUMMARY OF THE NEW VARIETY

The "August White" peach tree is characterized by producing late ripening, freestone fruit which have white flesh with a distinctive red skin coloration on the shoulders and along the suture at maturity and which possesses an appealing flavor. The new variety is ripe for commercial harvesting and shipment approximately August 20 to August 31 in the San Joaquin Valley of central California. The new variety is most closely similar to the "Champagne" peach tree (U.S. Pat. No. P.P. 4,865), but is distinguishable therefrom by the aforemented ripening date which is after that of the "Champagne" peach tree by about eight (8) days to two (2) weeks in the San Joaquin Valley. The fruit of the instant variety is much sweeter than that of the "Champagne" peach tree.

BRIEF DESCRIPTION OF THE DRAWING

The accompanying drawing is a color photograph showing fruit of the new variety, including a first in the top plan view displaying the shoulders and stem area; a second in bottom plan view showing the apex thereof; a third in side elevation showing the suture thereof; a fourth in side elevation rotated ninety degrees (90°) relative to the suture; and a fifth sectioned and laid open to expose the pit cavity in one section and the pit in its natural position in the pit cavity in the other section; and representative foliage of the new variety.

DETAILED DESCRIPTION

Referring more specifically to the pomological details of this new and distinct variety of peach tree, the following has been observed under the ecological conditions prevailing at the orchard of origin which is located near Dinuba, Calif. All major color code designations are by reference to Maerz and Paul, *A Dictionary of Color*, First Edition, 1930, McGraw Hill Book Co., Inc., New York, N.Y. Common color names are also occasionally employed.

TREE

Generally:

*Size.*—Medium.

*Vigor.*—Moderate.

*Chilling requirements.*—Normal for peaches in central San Joaquin valley of California.
*Productivity.*—Vigorous.
*Regularity of bearing.*—Uniform.

Trunk:
*Size.*—Medium.
*Surface texture.*—Medium.
*Color.*—Page 37, Plate 7, E1.
*Lenticels — numbers.*—Numerous.
*Lenticels — size.*—1.2 mm (0.0472 inches) to 1.5 mm (0.059 inches).

Branches:
*Size.*—Medium.
*Surface texture — mature.*—Medium.
*Surface texture — immature growth.*—Semi-smooth.
*Color — one year or older wood.*—Page 37, Plate 7, E2, between Elephant Skin and Pomei.
*Color — immature branches.*—Page 37, Plate 7, L9, Kazak Coptic.
*Lenticels — numbers.*—Numerous.
*Lenticels — size.*—1.5 mm (0.059 inches) to 2.00 mm (0.078 inches) by 4 mm (0.157 inches) to 9 mm (0.354 inches).

LEAVES

Size:
*Generally.*—Medium to large.
*Average length.*—181 mm (7.126 inches) to 187 mm (7.362 inches).
*Average width.*—44 mm (1.732 inches) to 48 mm (1.889 inches).

Form: Lanceolate.

Color:
*Upwardly disposed surface.*—Page 69, Plate 23, J7, Pologreen.
*Downwardly disposed surface.*—Page 67, Plate 22, H7, Garland Green.
*Leaf vein.*—Page 57, Plate 17, I7, Rivage Green.

Marginal form:
*Generally.*—Finely serrate.

Leaf vein:
*Thickness.*—15 mm (0.591 inches).

Glandular characteristics: Reniform.

Petiole:
*Size.*—9 mm (0.354 inches).
*Length.*—9 mm (0.354 inches) to 11 mm (0.433 inches).
*Thickness.*—2 mm (0.078 inches).
*Color.*—Page 57, Plate 17, 6K.

Stem glands:
*Form.*—Reniform.
*Position.*—Opposite each other.
*Color.*—Green.

Stipules: None.

FLOWERS

Flower buds:
*Size.*—8 mm (0.3149 inches) by 12 mm (0.472 inches).
*Surface texture.*—Glaucous.

Date of Bloom: Mar. 1, 1994.

Size:
*Generally.*—21 mm (0.827 inches) to 27 mm (1.063 inches), 21 mm (0.827 inches) to 23 mm (0.9055 inches).

Petals: Petal drop (Mar. 10, 1994).
*Color.*—Page 123, Plate 50, D4, near Cameo Pink.

FRUIT

Maturity when described: Ripe for commercial harvesting and shipment approximately August 20 to August 31 near Dinuba in the San Joaquin Valley of central California. The maturity date for the fruit of the "Champagne" peach tree in the San Joaquin Valley is, by contrast, about eight (8) days to two (2) weeks earlier than that of the new variety. At the time the fruit of the "Champagne" peach tree is ripe for commercial harvesting and shipping having firm flesh and bearing substantial coloration, the fruit of the instant variety is green and hard, bearing slight coloration substantially only in the suture line, and occasionally near the base.

Size:
*Generally.*—Moderate; on average about ten percent (10%) larger than mature fruit of "Champagne".
*Average diameter in the axial plane.*—9 cm (3.54 inches).
*Average diameter transverse in the suture plane.*—8.5 cm (3.34 inches).
*Average diameter transverse and at right angles to the suture plane.*—8.2 cm (3.228 inches).

Form:
*Uniformity.*—Globose.
*Symmetry.*—Symmetrical.

Suture:
*Generally.*—Shallow.

Ventral surface:
*Generally.*—Rounded slightly.

Stem cavity:
*Width.*—7 mm (0.275 inches) to 0.75 mm (0.295 inches).
*Depth.*—1.8 cm (0.709 inches) to 2.1 cm (0.827 inches).
*Length.*—1 cm (0.394 inches).
*Shape.*—Oval, elongated in suture plane.

Stem:
*Caliper.*—4 mm (0.157 inches).
*Length.*—7 mm (0.276 inches).

Apex: Short.

Pistil point: Lacking.

Skin:
*Thickness.*—Thin, less than 1 mm (0.039 inches).
*Texture.*—Medium.
*Blush color.*—Page 35, Plate 6, K3; the blush color extends in the suture line from the base to the apex of the fruit as coloration first begins with ripening. Coloration in the suture line is generally more pronounced than in the suture line of the fruit of the "Champagne" peach tree.
*Ground color.*—Page 45, Plate 11, I4.
*Tendency to crack.*—None observed.

Flesh:
*Flesh color.*—Page 45, Plate 9C1; close to pit cavity Page 33, Plate 5G6.
*Surface of pit cavity.*—Page 35, Plate 6, K6.
*Color of pit well.*—Page 35, Plate 6, L11.
*Juice production.*—Moderate.
*Flavor.*—Mild.
*Aroma.*—Pronounced.
*Texture.*—Medium.
*Fibers.*—Numbers — None.
*Ripening.*—Uneven on the shoulder and along suture.
*Eating quality.*—Fine. The fruit is much sweeter than that of "Champagne" peach tree, when tasted in each instance at full maturity.

Stone:

*Attachment.*—Freestone.
*Fibers — numbers.*—Few.
*Fibers — length.*—6 mm (0.236 inches) to 7 mm (0.276 inches).
*Size — length.*—35 mm (1.377 inches).
*Size — width.*—30 mm (1.181 inches).
*Size — thickness.*—2.5 mm (0.0984 inches).
*Form.*—Generally — Ovoid.
*Apex.*—Shape — Pointed.
*Color.*—Dry — Page 51, Plate 14, L12.
*Base.*—Shape — Straight.
*Sides.*—Generally — Equal.
*Ridges.*—Semi-sharp.
*Tendency to split.*—None observed.

Use: Commercial market (local and export).
Keeping quality: Medium to good.
Resistance to disease: Unknown.
Shipping and handling qualities: Shipping quality unknown.

Although the new variety of peach tree possesses the described characteristics noted above as a result of the growing conditions prevailing near Dinuba, Calif. in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described which is somewhat remotely similar to the "Champagne" peach tree (U.S. Pat. No. P.P. 4,865) of which it is a sport, but from which it is distinguished by producing white flesh fruit which are late ripening for commercial harvesting and shipment approximately August 20 to August 31, or about eight (8) days to two (2) weeks after the "Champagne" peach tree, in the San Joaquin Valley of central California and which have a sweeter flavor and a greater flesh coloration when compared therewith.

* * * * *

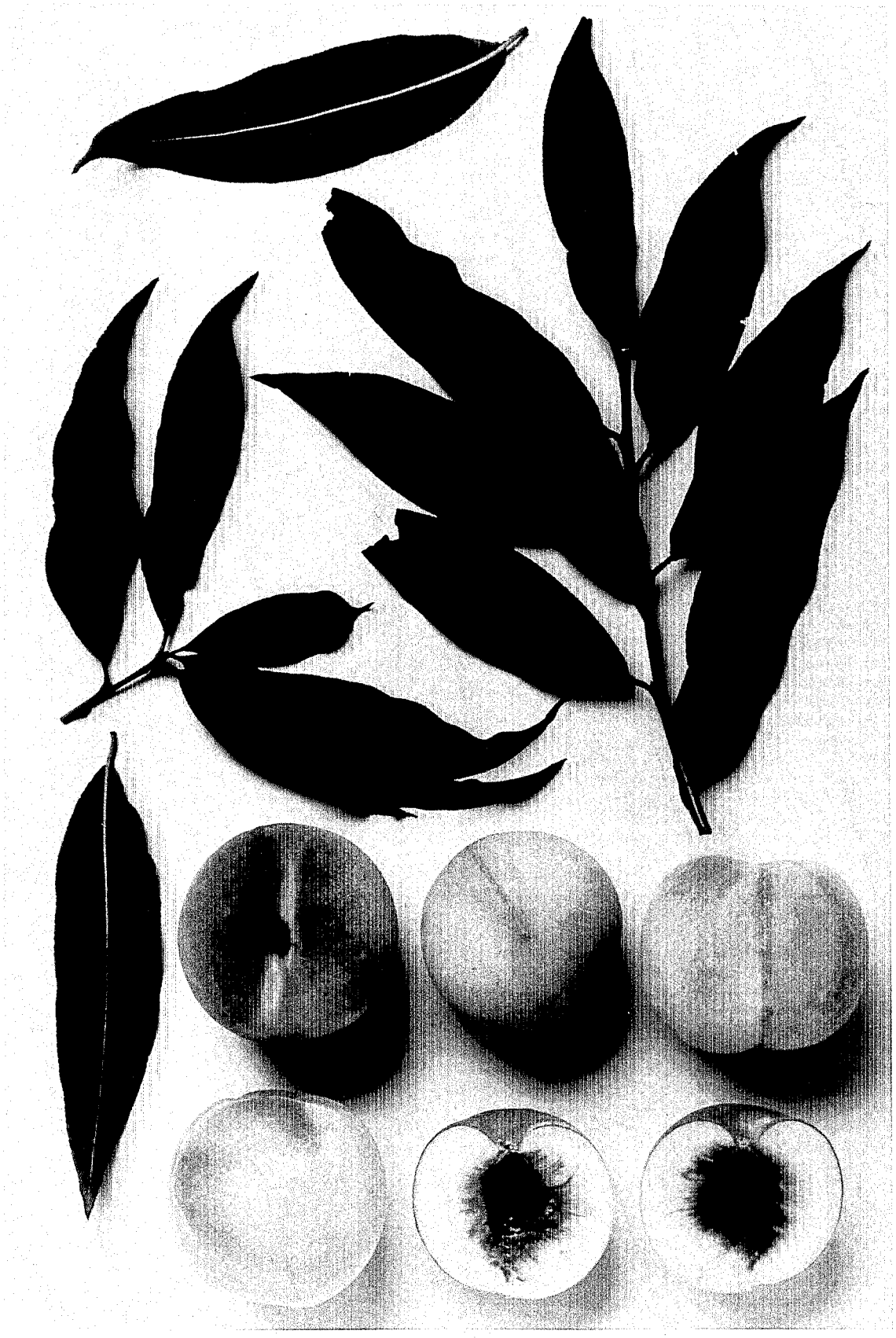

UNITED STATES PATENT AND TRADEMARK OFFICE

CERTIFICATE OF CORRECTION

PATENT NO. : PP 9784

DATED : January 21, 1997

INVENTOR(S) : Richard J. Marshall

It is certified that error appears in the above-identified patent and that said Letters Patent is hereby corrected as shown below:

Column 1, line 18, delete "contigent" and substitute ---contingent---.

Column 1, line 35, delete "is" (first occurrence) and substitute --in --.

Column 2, line 15, delete "aforemented" and substitute --aforementioned--

Column 4, line 66, after "of" insert --the --.

Signed and Sealed this

First Day of April, 1997

Bruce Lehman

BRUCE LEHMAN

*Commissioner of Patents and Trademarks*

*Attest:*

*Attesting Officer*